（12) United States Patent
Deptala et al.

(10) Patent No.: US 8,470,176 B2
(45) Date of Patent: Jun. 25, 2013

(54) ENCAPSULATION OF NANO-MATERIALS FOR FLUID PURIFICATION/SEPARATION

(76) Inventors: Alexander David Deptala, Spring Valley, CA (US); Daniel Alvarez, Oceanside, CA (US); Arthur Deptala, Spring Valley, CA (US)

( * ) Notice: Subject to any disclaimer, the term of this patent is extended or adjusted under 35 U.S.C. 154(b) by 506 days.

(21) Appl. No.: 12/705,621

(22) Filed: Feb. 14, 2010

(65) Prior Publication Data

US 2011/0201041 A1 Aug. 18, 2011

(51) Int. Cl.
*B01D 39/00* (2006.01)
(52) U.S. Cl.
USPC .......... 210/600; 210/500.25; 210/500.27; 210/506; 55/522
(58) Field of Classification Search
USPC .......... 210/635, 500.1, 500.25, 500.27, 210/503, 506, 679, 600; 55/522
See application file for complete search history.

(56) References Cited

U.S. PATENT DOCUMENTS

| 5,767,167 | A  | * | 6/1998 | Ferry ........................ 521/64 |
| 5,945,084 | A  | * | 8/1999 | Droege .................. 423/447.4 |
| 8,132,667 | B2 | * | 3/2012 | Zimmermann ............. 206/0.7 |
| 2007/0031321 | A1 | * | 2/2007 | Alvarez et al. ............ 423/490 |
| 2010/0176053 | A1 | * | 7/2010 | Adams et al. ............. 210/614 |

FOREIGN PATENT DOCUMENTS

FR 2910458 A1 * 6/2008

* cited by examiner

*Primary Examiner* — Fred Prince
(74) *Attorney, Agent, or Firm* — Oakwood Law Group, LLP; Jie Tan

(57) ABSTRACT

Disclosed is an apparatus and method whereby small particle nano materials may be contained in a highly functional package for fluid separation and/or purification applications. The package consists of an aerogel material which uniformly surrounds the nano-particles. The aerogel may be composed of carbon, silicon, or silicon oxide or other suitable materials. The morphological features of the aerogel may be tailored specifically towards fine particle and ultrafine particle containment while maintaining uniform fluid flow in separation and purification processes. The aerogel may be bonded to a suitable rigid housing by chemical or mechanical means.

10 Claims, 7 Drawing Sheets

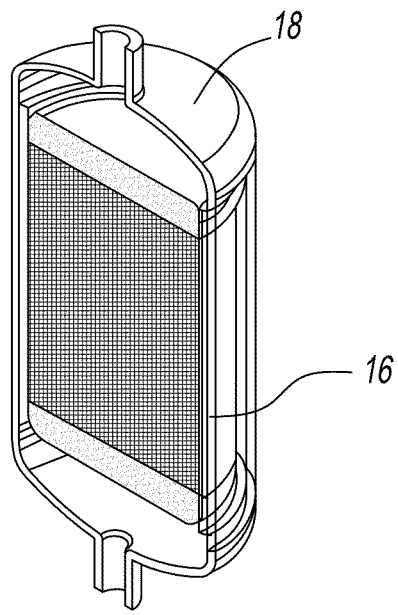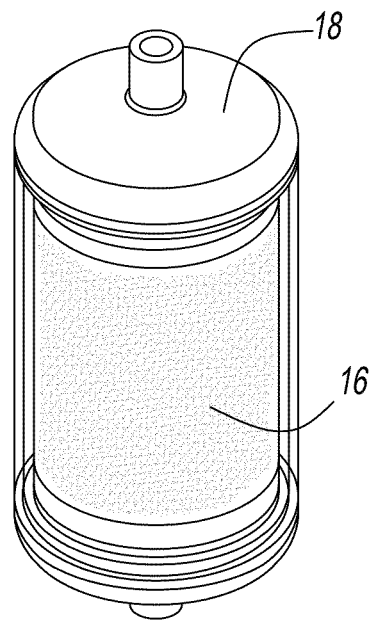
FIG. 3A    FIG. 3B
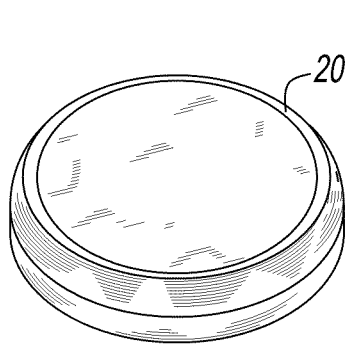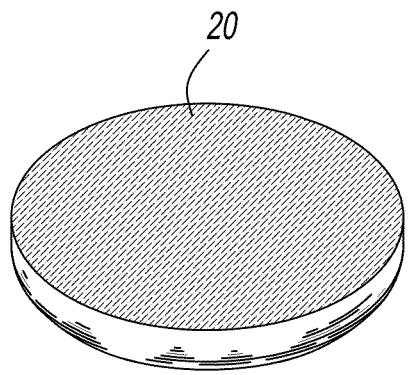
FIG. 4A    FIG. 4B

ENCAPSULATION OF NANO-MATERIALS FOR FLUID PURIFICATION/SEPARATION

BACKGROUND OF THE INVENTION

1. Field of the Invention

The present invention relates generally to nano-particles and more particularly to nano-particles surrounded by a gel for fluid separation and/or purification applications.

2. Description of Related Art

Over the last two decades immense progress has been made in the synthesis of nano-materials. These materials have morphological features on the nano-scale which lead to special chemical and physical properties. A sub-classification of nano-materials is nano-particles which are minute objects that function as wholes units. Nano-particles are generally classified according to sizes ranging from 1-2500 nanometers. These materials have been structurally engineered and are characterized by tremendously high surface areas' (m2/gram) and often have tremendously high pore volume (ml/ml). Particle size (length and width), pore size, and directionality can be manipulated through novel synthetic methods. Specific chemical and physical properties can be structurally integrated through choice of elemental substituent's and dimensional features. The most well known among these materials are buckyballs, single and double walled carbon nano-tubes, silicon and silicon dioxide nano-wires. Several others exist that are of non-uniform shape or have extremely small particle size on the order of nanometers. More extensive are the highly porous inorganic analogues such as nickel sponge, and a considerable variety of other inorganic metals and metal oxides.

Several potential applications of these materials exist across several industries. Immediate applications can be found in chemical, biological, pharmaceutical, semiconductor, energy and environmental fields for separation and purification of fluid materials. These range from crude separation of raw materials to final purification processes down to parts-per-trillion purity levels.

These may involve chemical recycling, energy storage, analyte separation in biological samples, high purity purification for semiconductor processes, water remediation, air pollution control, metal capture in the nuclear industry, removal of toxic materials for human safety, microbial contamination sensing and control, as well as controlled release drug delivery.

Practical application of these materials has found very limited use. Some of this may be attributed to a lack of availability. However, other problems exist such as small particle agglomeration and complete particle containment. Some carbon based materials have been granulated, pressed into blocks, or woven into fabrics. However, the rendering of these materials into a practical, useful form remains a significant challenge.

Particle sizes of carbon and silicon based materials can be as minute as 20-300 nanometers. Thus, containment of these materials in a functional form for fluid separation and purification applications is problematic. From the standpoint of material retention, it is imperative that particles not be released into the fluid stream. Moreover, key to the successful utilization of these nano-materials is exploitation of the materials' entire effective surface area. Here, it is key that fluid flow runs uniformly throughout the interior pores of the material as well as across the entire outer surface. Therefore, proper material packaging is essential. Functional considerations also need to be taken into account. Pressure drop across the entire materials packaging assembly must be kept to a minimum. In other instances, separations must be conducted in multiple steps and it may be necessary to position diverse nano-materials separately.

What is needed is an apparatus and method for providing small nano-particles that can be contained in a functional package for fluid separation and/or purification applications.

SUMMARY OF THE INVENTION

In an exemplary embodiment of the present invention, there is disclosed an apparatus adapted for separation or purification of fluid materials comprising:

an aerogel material; and said aerogel material is a covalently bonded porous three dimensional network;

wherein said aerogel is a porous microcellular foam substance having a density of 0.1 grams per square centimeter to 0.7 grams per square centimeter and an area-to-mass ratio of 100 square meters per gram to 3000 square meters per gram.

In an exemplary embodiment of the present invention, there is disclosed a method for separating or purifying fluid materials comprises:

providing an aerogel material; and encapsulating nanometer sized particles within said aerogel;

wherein said aerogel material is a covalently bonded, porous three dimensional network; and wherein said aerogel is a porous microcellular foam substance having a density of 0.1 grams per square centimeter to 0.7 grams per square centimeter and an area-to-mass ratio of 100 square meters per gram to 3000 square meters per gram.

In a further exemplary embodiment of the present invention, nano sized particles can be encapsulated within aerogel materials and separated by insulating materials to provide a device suitable for electrical energy storage. The device can be used for large scale stationary applications such as solar energy storage or may be a small portable apparatus where two or more distinct types of nano sized particles are capable of storing electrical energy in the form of chemical energy are separated by insulating materials. The entire materials assembly is encapsulated by the aerogel.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIGS. 3A and 3B are perspective views of a half cylinder and a full cylinder of nano-material encapsulated within an aerogel which is encased in a housing suitable for practical use;

FIGS. 4A and 4B are perspective views of nano-materials incorporated into an aerogel and molded or sculpted to form a plug shape;

DESCRIPTION OF THE PREFERRED EMBODIMENT

Figures 1A, 1B:
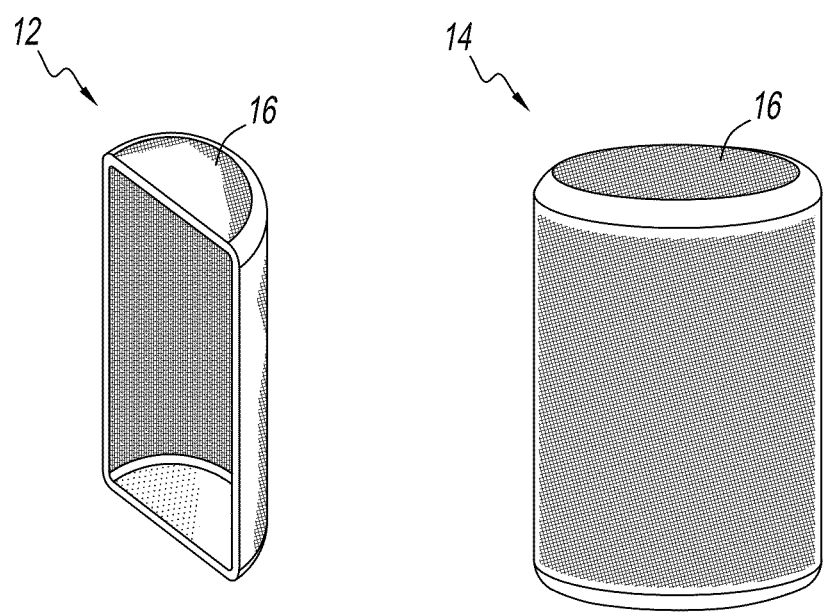
FIGS. 1A and 1B are perspective views of a half cylinder and a full cylinder of nano-material contained within an aerogel in accordance with the principles of the invention.
Figure 2A:
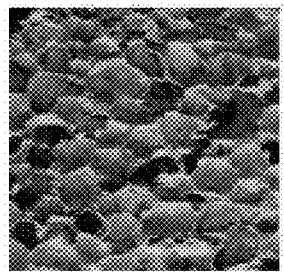
FIGS. 2A-2H are magnified views of eight morphological features of representative aerogels in accordance with the principles of the invention.
Figure 2B:
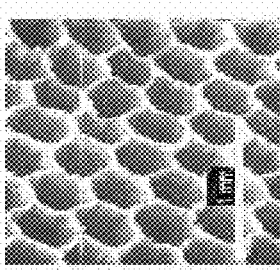
Figure 2C:
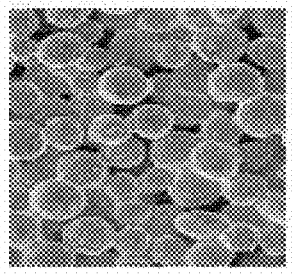
Figure 2D:
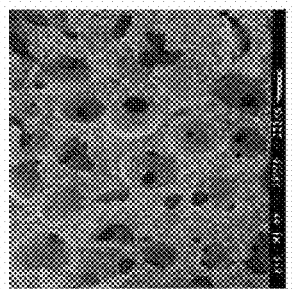
Figure 2E:
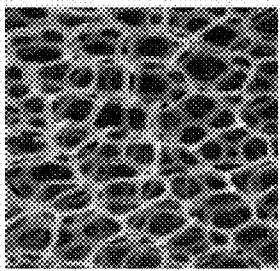
Figure 2F:
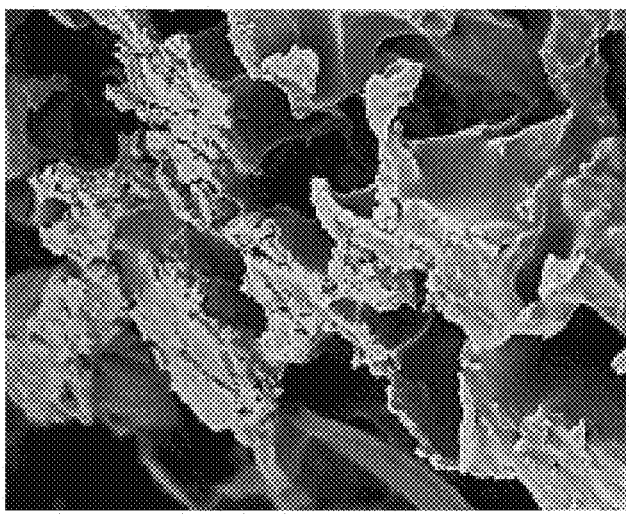
Figure 2H:
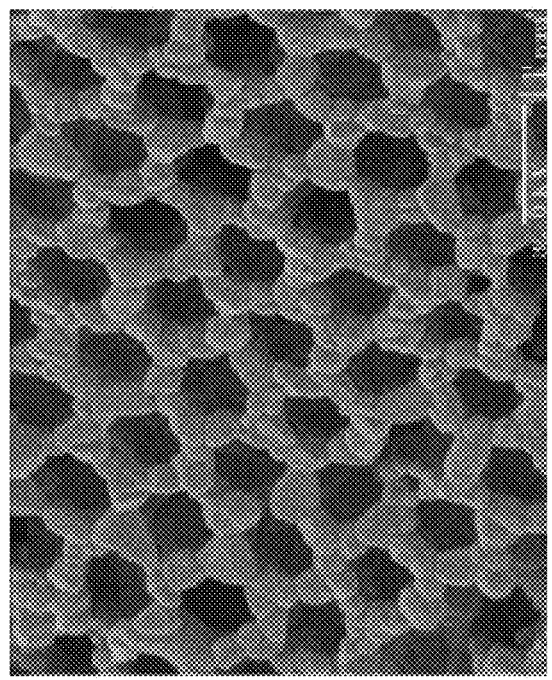
Figure 2G:
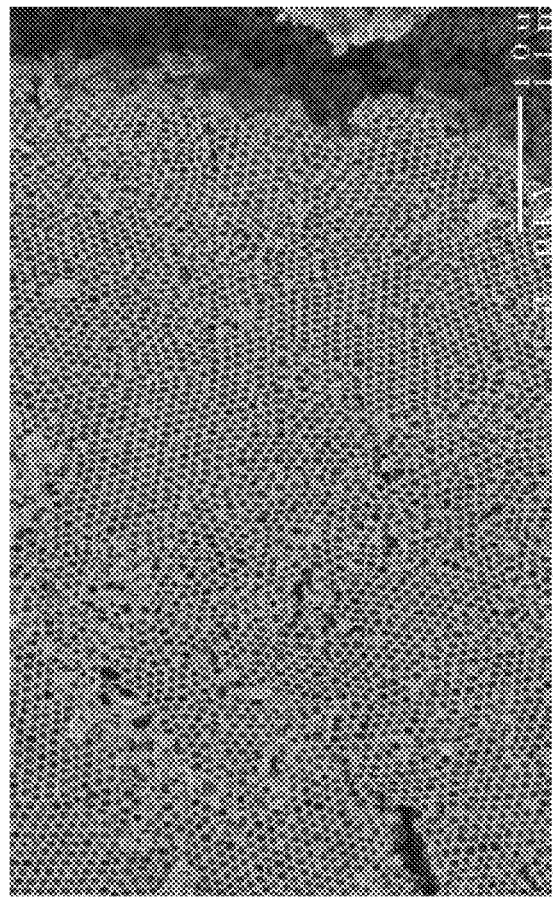

There is described an apparatus and method where small particle nano-materials are contained in a highly functional package for fluid separation and/or purification applications. The package consists of an aerogel material which uniformly surrounds the nano-particles. Referring to FIGS. 1A and 1B, there are shown perspective views of a half cylinder 12 and a full cylinder 14 of nano-particles 16 contained within an aerogel. The aerogel can be composed of carbon, silicon, silicon oxide or other suitable materials. In some instances these materials may be reinforced with carbon based polymers, carbon fibers, inorganic additive material or other such materials that enable them to have mechanical strength to withstand elevated fluid pressures.

Referring to FIGS. 2A-2H, there are shown morphological features of eight representative aerogels in accordance with the principles of the invention. An aerogel is defined as a microcellular foam substance that is highly porous, low in density (0.1-0.7 $g/cm^2$) and has an area-to-mass ratio of 100-3000 $m^2/g$. Aerogels are comprised of covalently bonded, nanometer-sized particles that are arranged in a 3-dimensional network. The aerogel is typically composed of carbon, but can also consist of other similarly bonded suitable compositions. These materials have highly porous channels where pore sizes range from 1-300 nanometers in diameter. The aerogel chemical composition, microstructure, and physical properties can be controlled at the nanometer scale, giving rise to unique fluid flow and containment attributes. These aerogels can be produced from freeze drying processes or supercritical fluid drying processes. Aerogels materials of this type are shown in FIGS. 2A-2H and are available from Reade Advanced Materials, Inc., located in Sparks, Nev.

Referring to FIGS. 3A and 3B, there are shown cutaway perspective views of the nano-material 16 of FIGS. 1A and 1B encapsulated in an aerogel and encased in a housing 18 to provide an apparatus that is suitable for practical use. The housing 18 can be composed of Teflon, stainless steel, aluminum or any other material where the nature of a specific separation and/or purification application dictates the proper material choice. In an embodiment of the invention, the aerogel may be bonded to a suitable rigid housing by chemical or mechanical means. Seals can be made by plastic welding techniques, metal welding techniques or with the use of adhesives. In another embodiment a mechanical seal can be provided by using an o-ring or similar pressure sealing device. Adhesion of the aerogel to the housing may also be obtained by the use of a mutually compatible solvent followed by a solvent removal.

Pore sizes of the aerogels can be specifically tailored by solvent evaporation processes. The choice of solvent with regard to boiling point and polarity properties can be used to manage bulk material porosity as well as individual pore size. In general, a slower evaporation rate leads to a higher bulk porosity of the aerogel. Individual pore size can also be controlled by solvent molecular size and polarity. Here solvent polarity that is similar to that of carbon, silicon, silicon oxide, metal or metal oxide materials lead to stronger intermolecular interactions which in turn can lead to large pore sizes. Solvent polarity that is distinct from the bulk material can lead to faster evaporation rates and smaller pore sizes. The net result is that pore sizes can be tailored to maximize the containment properties of the resultant aerogel with respect to the particle size of the material that is to be contained.

Concerning particle retention, it is crucial that the contained nano-particles not be released into the fluid stream. The aerogel is a 3-dimensional network of pores, where a variety of pores sizes is attainable. Aerogels can be tailored to contain fine particles which are classified by diameter sizes of 100-2500 nanometer. More significant is that aerogel pore size can be tailored to contain ultrafine particles which are classified as having diameters of 1-100 nanometers. In all cases it is necessary to tailor the pore size and the three dimensional network of pores of the aerogel to prevent nano-particles from being released into the fluid stream.

At the same time the morphological features of the aerogel should allow a uniform fluid flow across and throughout the nano-material contained within. Pores sizes may in some instances be smaller than the particle size of the material being contained, thereby allowing for fluid flow through the aerogel but disallowing passage of the nano-particles. In other embodiments, the pore size of the aerogel can be equal to or larger than the particle size of the contained nano-particles. In this embodiment the 3-dimensional nature of the aerogel porous network can prevent release of the nano-particles into the fluid stream.

Pore size of the aerogel can be tailored to minimize pressure drop of the fluid. In this embodiment it is desirable to maintain the pressure at the outlet side of the separation and/or purification vessel close to the pressure at the inlet side. While it is desirable to keep the outlet pressure within 20% of the inlet side, it is preferable to have an outlet pressure that is within 3% of the inlet side. Regarding pressure drop properties, aerogel pore size and bulk porosity can be varied to allow free flow of a fluid. In addition, the chemical nature of the aerogel may be adjusted to minimize surface interactions between the fluid and the aerogel surface. In this embodiment the chemical nature of the surface can be adapted to provide efficient fluid flow. In some embodiments it may be preferable to use an aerogel material of high polarity, such as metal oxides materials. In other embodiments minimization of surface interaction may be accomplished through the use of non-polar aerogels such as elemental carbon, silicon, or composites of such materials. Yet other embodiments may call for the incorporation of a small percentage of the contained nano-material into the aerogel.

With regard to pressure drop, it may also be desirable to control the aerogel thickness. In this embodiment aerogels of lower thickness may provide lower pressure drop. Thickness may be used in combination with pore size. If a pore size that is smaller than that of the contained nano-material particle size is to be used, less dependence for containment is placed on the 3-dimensional porous network. In this embodiment, a lesser aerogel thickness may be utilized.

In cases where a small percentage of the nano-material is incorporated into the aerogel, the aerogel itself may also become active towards fluid separation or purification. In this embodiment the aerogel serves as a barrier which prevents release of the nano-particles as well as augmenting the separation and/or purification properties of the contained nano-material.

Referring to FIGS. 4A and 4B, there are shown perspective views of nano-materials incorporated into an aerogel which is molded or sculpted to form a plug shape 20 for use in separation and/or purification applications. A specific chemical composition of this concept may comprise the incorporation of carbon nano-tubes into porous carbon aerogels.

A further embodiment of the invention is the inherent fluid diffusion properties of the aerogel. Fluid flow properties that result from tailoring the three dimensional porous network may also provide uniform fluid flow with minimal pressure drop in the presence or absence of purification and/or separation requirements. In this embodiment uniform fluid flow may be achieved in situations where rapid changes in flow rate are encountered. Uniform fluid flow may also be maintained in situations where rapid changes in fluid pressure or fluid exposure to a vacuum are encountered. In an embodiment where fluid purification and/or separation is not required, the preferred form of the aerogel may be that of the molded or sculpted plug.

Figure 5A:
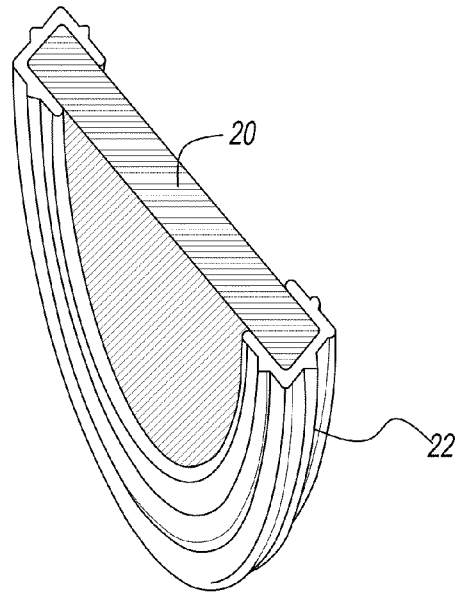
FIGS. 5A and 5B are perspective views of the molded or sculpted plug of FIGS. 4A and 4B over-molded and encased in Teflon or other similar material.
Figure 5B:
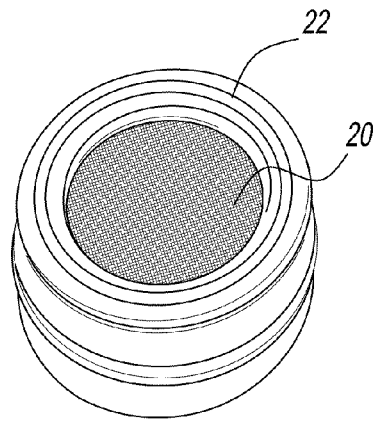

Referring to FIGS. 5A and 5B, there is shown perspective views of the molded or sculpted plug 20 over-molded and encased in Teflon or other similar material 22. An over mold of this type allows for the aerogel plug to be placed in a housing suitable for practical use where the over-mold may be bonded to the aerogel plug by chemical or mechanical means.

In an embodiment the nano-material, a polymeric additive, or an inorganic additive may comprise part of the aerogel. These additives may impart mechanical strength to the overall aerogel structure which will allow the aerogel to be used in applications where fluid pressures need to be maintained at elevated pressures, reduced pressures or in a vacuum. The additives can prevent collapse of the porous structure in situations where rapid changes in pressure may occur.

Another aspect of the invention relates to the use of multiple nano-materials, where nano-materials need to be separated. In this embodiment an aerogel may be used to form multiple compartments within a housing device.

Figure 6A:
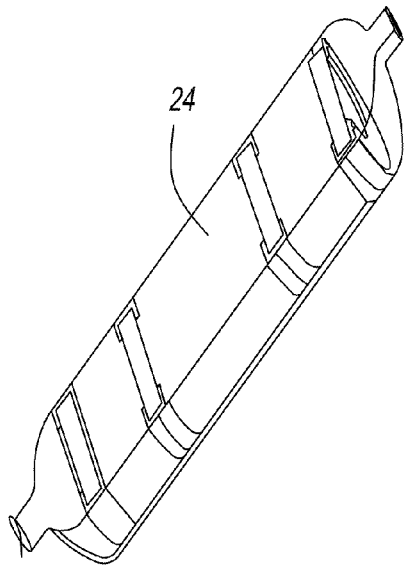
FIGS. 6A and 6B are perspective views of a housing encasing aerogel compartments, where the housing has 3 compartments for physical separation of discrete nano-materials.
Figure 6B:
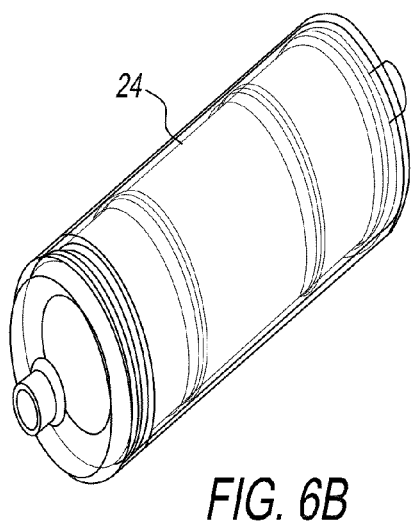

Referring to FIGS. 6A and 6B, there are shown perspective views of a housing 24 bonded to aerogel compartments, where the aerogel has three compartments for physical separation of discrete nano-materials. An apparatus of this type allows for sequential separation and/or purification of fluids from one another based on chemical or physical properties of each individual nano-material. An apparatus of this type may be constructed step-wise by filling the first compartment with the desired nano-material, forming a seal which encloses this compartment, followed by the addition of distinct nano-materials to additional compartments. The compartments may be sealed by chemical or physical means individually after filling is completed. The number of compartments will be dictated by the complexity of the separation process. The apparatus of this type can be used for the purification of a fluid for use in semiconductor manufacturing, for use in water remediation, for use in separation of chemicals for recycling, for use in separation of analytes in biological samples, for use in air pollution control, for use in metal capture in the nuclear industry, for use in removal of at least one toxic chemical, for use in microbial sensing and control, for use in controlled release drug delivery, and for use in pharmaceutical manufacturing.

Figure 7A:
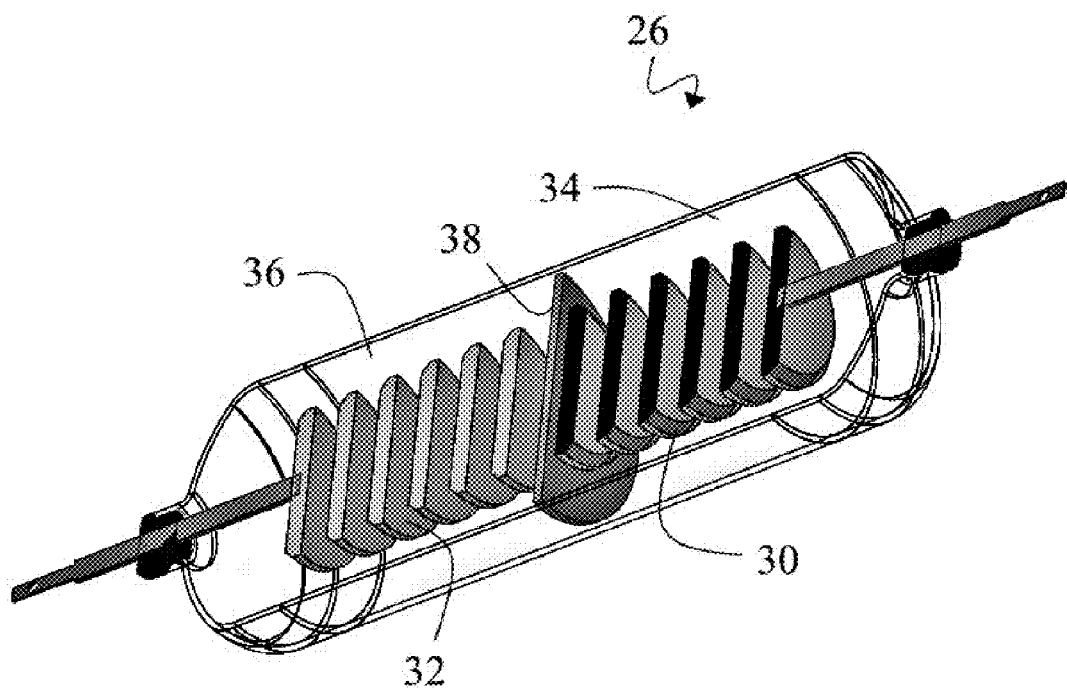
FIGS. 7A and 7B are perspective views of a half cylinder and a full cylinder of a device having two distinct nano size particles capable of storing electrical energy in the form of chemical energy where the two distinct nano size particles are separated by insulating materials and the entire materials assembly is encapsulated by the aerogel in accordance with the principles of the invention.
Figure 7B:
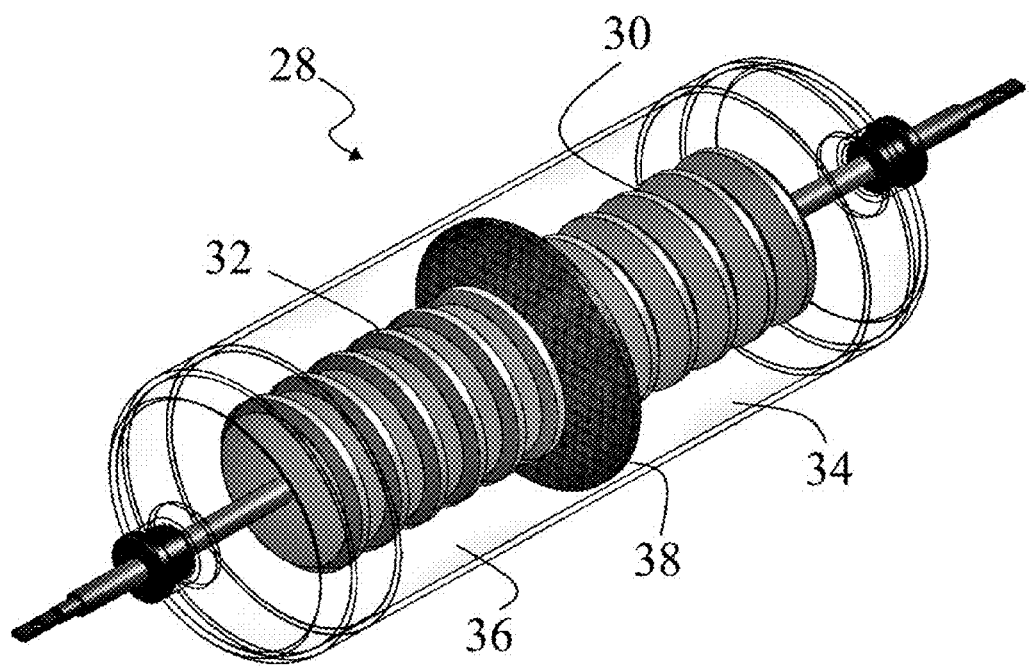

Referring to FIGS. 7A and 7B, there are shown perspective views of a half cylinder 26 and a full cylinder 28 of a device having two distinct nano size particles 30, 32 capable of storing electrical energy in the form of chemical energy where the two distinct nano size particles are separated by insulating materials 38 which are encapsulated by aerogel materials 34, 36 in accordance with the principles of the invention. The aerogel material can contain an electrolyte, or itself be composed of a material with electrolyte properties in order to facilitate the conversion of chemical to electrical energy.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. An apparatus adapted for separation or purification of a fluid material comprising:
   a sealed housing having an housing inlet, a housing outlet and a sealed first side wall;
   at least one aerogel casing encapsulating an aerogel foam, mounted inside said housing, said aerogel casing having an upper surface with a casing inlet, a lower surface with a casing outlet, and a casing side surface, said upper surface being disposed to face said housing inlet; said lower surface being disposed to face said housing outlet, and said casing side surface being facing said first side wall;
   wherein said aerogel foam is made of an aerogel material, and said aerogel material forms a covalently bonded porous three dimensional network, and a plurality of 1-2500 nanometer nanoparticles specific for separation or purification of said fluid material are stored inside said porous three dimensional network,
   thereby in use said fluid material flows from said housing inlet through said casing inlet, said aerogel foam, said nanoparticles, said casing outlet and said housing outlet.

2. The apparatus of claim 1 wherein said aerogel material includes a polymeric or an inorganic additive material to provide mechanical strength.

3. The apparatus of claim 1 wherein said aerogel material comprises a carbon or a silicon material and has pore sizes between one nanometer and 300 nanometers.

4. The apparatus of claim 1 wherein said first aerogel casing is in a sculpted or molded plug form.

5. The apparatus of claim 4 wherein said aerogel casing is made of Teflon, stainless steel or aluminum by chemical or mechanical means.

6. The apparatus of claim 4, further comprising another aerogel casing containing a different set of nanoparticles, stacked within said housing.

7. The apparatus of claim 1 wherein said sealed housing is separated into a plurality of individual compartments.

8. A method for separating or purifying a fluid material comprises:
   forming a first aerogel foam within a first sealed casing structure wherein said first aerogel foam is a porous three dimensional network with an aerogel material, said first casing structure has a first casing inlet and a first casing outlet, said encasing structure is stacked within a sealed housing having a housing inlet and a housing outlet;
   encapsulating first nanometer sized nanoparticles made specific for separating or purification of said fluid material within said aerogel foam; and
   flowing said fluid material into said housing inlet to said first casing inlet, and flowing through said first aerogel foam and said first nanoparticles out from said first casing outlet to be separated or purified by said nanoparticles.

9. The method of claim 8 wherein said nanoparticles are specific for the purification of a chemical or a biological component from said fluid material.

10. The method of claim 8, further comprising the steps of:
    stacking a second sealed casing structure encapsulating a second aerogel foam containing second nanometer sized nanoparticles of second property for separating or purification of said fluid material; and
    further flowing said fluid material output from said first casing outlet through said second encasing structure and said second nanoparticles to be further separated and purified.

* * * * *